Figure 1:
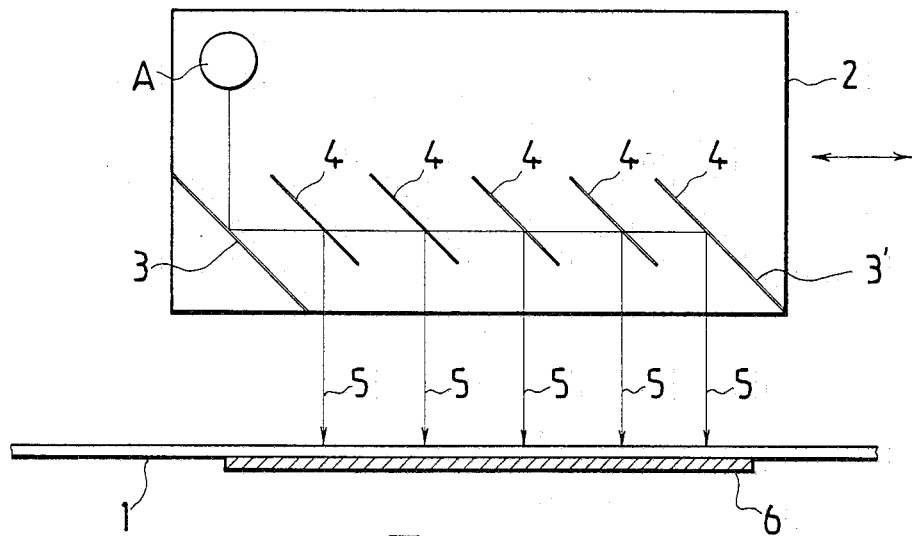

United States Patent [19]

Puumalainen

[11] Patent Number: 4,595,840

[45] Date of Patent: Jun. 17, 1986

[54] PROCEDURE AND MEANS FOR OBSERVING STREAKS IN THE MACHINE DIRECTION IN PAPER OR IN ITS COATING

[75] Inventor: Pertti Puumalainen, Kuopio, Finland

[73] Assignee: Enso-Gutzeit Oy, Helsinki, Finland

[21] Appl. No.: 624,933

[22] Filed: Jun. 27, 1984

[30] Foreign Application Priority Data

Jun. 28, 1983 [FI] Finland ................................ 832347

[51] Int. Cl.⁴ ............................................ G01N 21/88
[52] U.S. Cl. .................................... 250/572; 356/431
[58] Field of Search ................. 356/430, 431; 250/572, 250/562, 563

[56] References Cited

U.S. PATENT DOCUMENTS

| | | | |
|---|---|---|---|
| 3,655,989 | 4/1972 | Robinson | 250/572 |
| 3,754,146 | 8/1973 | Chow | 250/563 |
| 4,274,747 | 6/1981 | Van Beeck et al. | 250/563 X |
| 4,338,032 | 7/1982 | Bardsley et al. | 250/572 |
| 4,450,359 | 5/1984 | Ross et al. | 250/572 |
| 4,455,086 | 6/1984 | West | 250/572 X |

FOREIGN PATENT DOCUMENTS 1170179 11/1969 United Kingdom ................. 250/572

Primary Examiner—Shrive P. Beck
Attorney, Agent, or Firm—Toren, McGeady, Stanger, Goldberg & Kiel

[57] ABSTRACT

The present invention concerns a procedure and a means for observing streaks in the machine direction in paper or in its coating, on a web (1) in continuous motion, a measuring box (2) being moved reciprocatingly across the paper web, from a light source (A) therewithin light being conducted against the paper web (1) in the form of separate light beams (5) spaced uniformly in the direction across the web, whereafter the intensities of the transmission beams from the paper or of the reflected beams from the coating are measured each separately by means of a detector (7) placed in the path of each light beam (5), the deviation of intensity found by the detector being automatically recorded in time and in space, whereafter the deviations of intensity coming later in succession from other detectors (7) are superimposed in time, whereby when similar intensity deviations come from the majority of the different detectors, the deviation must have been caused by a streak in the machine direction across which the equivalent number of light beams (5) has passed.

2 Claims, 2 Drawing Figures

PROCEDURE AND MEANS FOR OBSERVING STREAKS IN THE MACHINE DIRECTION IN PAPER OR IN ITS COATING

The present invention concerns a procedure and a means for observing streaks running in the machine direction in paper or in its coating, on a continuously moving paper web.

The paper web produced on a paper machine may be marked with streaks in the machine direction, i.e., in the direction in which the paper web is propagated, for various reasons. So-called positive streaks, presenting more material on the surface of the paper than in the close vicinity, may result for instance from the headbox of the paper machine at one point in the cross-machine direction supplying more stock onto the wire than at adjacent points. In coating machines, in which mineral pigment is spread by the aid of a blade on the paper web, a chipped blade admits more pigment through the existing gap onto the surface of the paper web, whereby a streak may be produced which is sharply salient from its environment. Such streaks cause trouble in the calender, where the paper web is powerfully compressed between rolls. The consequence may in fact be damage to a whole calender roll so that the paper cannot be shipped to the customer. Negative streaks, which are grooves or scores in the surface of the paper or in its coating, are usually produced in the way that a piece of foreign matter sticks to the lip slice or the upper blade of the headbox, producing in the surface a streak with greater depth than the adjacent area. The penetration of printer's ink into such a streak is unsatisfactory, and printing defects occur in the paper at the site of the streak.

Presently, no automatic method exists for observing streaks, the detection of streaks being based on visual observation of the paper.

The object of the present invention is to provide an automatic procedure and a means for observing a streak on a moving web by using separate light beams directed across the web.

The procedure and the means of the invention are characterized by that which is stated in the claims following below.

Figure 2:
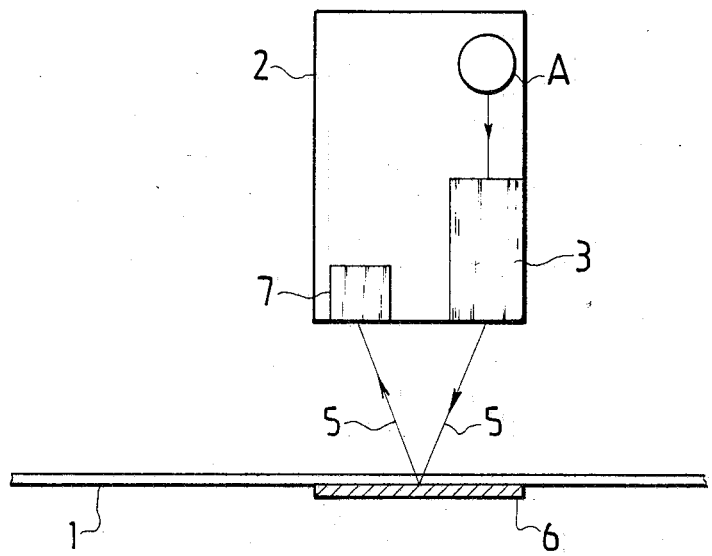

The invention is described in the following in detail by the aid of a drawing wherein FIG. 1 presents an embodiment viewed in the direction of travel of the paper web, and FIG. 2 shows the same in elevational view, or in the cross-machine direction of the web.

An apparatus embodiment of the invention is the means depicted in FIG. 1, where above the paper web 1 has been placed a box 2 which may be moved reciprocatingly in the direction across the web, as indicated by a double arrow. At one end of the box 2, a mirror 3 has been placed therewithin at an angle of 45° and light is made to impinge thereon from a light source A, which light may be laser light for instance. The light is reflected by the mirror 3 horizontally towards a mirror 3 at the other end of the box 2, this latter mirror in turn reflecting the light downwards.

In order to distribute the light uniformly in the transversal direction of the paper web 1 with the purpose of finding streaks, the light from the mirror 3 has been divided by the aid of partly transparent mirrors 4 into light beams with approximately equal intensity which are directed at an angle of about 90° against the paper web 1 and in the direction at right angles to it are uniformly spaced. Under the paper web 1, in the immediate vicinity thereof, a mirror 6 has been placed across the web, by the aid of which the light that has passed through an uncoated paper is reflected back again through the paper web, and it is therefore not absolutely necessary to move a detector box in identical manner under the web. The intensity of this transmission radiation is determined by means of a detector 7 behind each light beam 5 (FIG. 2). If there is a streak in the paper which, as has been said, in uncoated paper may be due to the headbox of the paper machine at one spot in the transversal direction of the web delivering more stock or less stock than in the vicinity, the intensity of the transmission radiation received at this point from the paper web is altered when one of the light beams 5 from the box 2 hits said streak and passes thereacross. Any such deviation is recorded in time and space, this being enabled by the box 2 moving across the paper web 1 at a given uniform velocity. If all detectors 7 placed temporally in succession, their displays being with the aid of a computer shifted in time to be superimposed, register a similar intensity disturbance, there is a streak in the machine direction in the paper web 1, the location of which has thus been recorded in the location where the first light beam 5 to detect the deviation was positioned at that time and which the computer has stored in its memory with the aid of the detector 7. In practice it is enough that a deviation occurs in the greater part (in 90%) of the detectors. The above-described measurement, based on the movement of the box 2 across the web, may be performed on coated papers as well. In this case, however, the reflection of light from the surface of the coating is measured and the measured intensities are processed as in the case of transmission. In the apparatus embodiments of the procedure of the invention, the light beams 5 may be produced even otherwise than has been presented in FIG. 1. An advantageous way is to conduct the light emitted by a light source A, either ordinary or laser light, into a bundle of optical fibres, each of them being fixed in its own position in the transversal direction of the box 2. Discrete light beams 5 may of course also be produced in that on the box 2 are mounted as many individual light sources as the width of the web requires and each such source directs its own light beam 5 against the paper web.

It is clearly evident from the foregoing that the procedure and means of the invention are not confined to the embodiment presented in the drawing and that they may instead be modified within the scope of the claims following below.

I claim:

1. A procedure of detecting streaks extending in the machine direction of a paper web in which the paper web is moved continuously in said direction and the detecting is carried out with the use of a measuring box having a path of travel in a direction transverse to that of the movement direction of the web, said box being provided with means for producing a number of mutually spaced light beams of substantially equal intensities spaced from each other in the direction of the path of travel of the box, and said box being further provided with a number of detectors adapted to measure the intensities of light beams entering the box, the detection comprising the steps of moving the measuring box along its path of travel across the moving web, producing the number of light beams and directing the light beams from the measuring box to the web, reflecting the light beams which have met the web to the detectors in the measuring box and measuring the intensities of the reflected beams so that a streak in the machine direction of the web is detected as a sequence of similar disturbances in the intensities measured by the different detectors, caused by sequential crossing of the mutually spaced light beams and the detectors over the streak, and wherein reflection of the beams is achieved by means of a mirror facing the path of travel of the measuring box on the other side of the moving web.

2. An apparatus for detecting streaks in the machine direction of a paper web, the apparatus comprising a measuring box placed adjacent to the web which is continuously moved in its machine direction, said box having a path of travel in a direction transverse to that of the movement of the web, and said box being provided with means for producing a number of light beams of substantially equal intensities spaced from each other in the direction of the path of travel of the box and for directing the beams as produced to the moving web, and said box being further provided with a number of detectors for measuring the intensities of the light beams as reflected to the detectors after meeting the web, and the apparatus further comprising a mirror for reflecting the light beams to the detectors, the mirror being placed to face the path of travel of the measuring box on the other side of the moving web.

* * * * *